United States Patent
Watanabe et al.

(10) Patent No.: US 11,245,764 B2
(45) Date of Patent: Feb. 8, 2022

(54) SERVER APPARATUS, ODOR SENSOR DATA ANALYSIS METHOD, AND COMPUTER READABLE RECORDING MEDIUM FOR UNFIXED ODOR ANALYSIS TARGETS

(71) Applicant: NEC CORPORATION, Tokyo (JP)

(72) Inventors: Junko Watanabe, Tokyo (JP); Riki Eto, Tokyo (JP); Hidetaka Hane, Tokyo (JP); Shigeo Kimura, Tokyo (JP); Shintarou Tsuchiya, Tokyo (JP)

(73) Assignee: NEC CORPORATION, Tokyo (JP)

( * ) Notice: Subject to any disclaimer, the term of this patent is extended or adjusted under 35 U.S.C. 154(b) by 6 days.

(21) Appl. No.: 16/753,403

(22) PCT Filed: Oct. 2, 2018

(86) PCT No.: PCT/JP2018/036955
§ 371 (c)(1),
(2) Date: Apr. 3, 2020

(87) PCT Pub. No.: WO2019/069958
PCT Pub. Date: Apr. 11, 2019

(65) Prior Publication Data
US 2020/0322435 A1    Oct. 8, 2020

(30) Foreign Application Priority Data

Oct. 3, 2017   (JP) .............................. JP2017-193901

(51) Int. Cl.
*H04L 29/08*      (2006.01)
*G01N 33/00*      (2006.01)
(Continued)

(52) U.S. Cl.
CPC ......... *H04L 67/12* (2013.01); *G01N 33/0031* (2013.01); *G01N 33/0098* (2013.01);
(Continued)

(58) Field of Classification Search
CPC ........... G01N 33/0031; G01N 33/0098; G01N 33/4972; H04L 67/12; H04L 67/2828; H04L 67/2895
See application file for complete search history.

(56) References Cited

U.S. PATENT DOCUMENTS

2013/0244336 A1*  9/2013  Mayer ................ G01N 33/0031
                                                           436/147
2015/0308993 A1* 10/2015  Fukui ................. G01N 33/0034
                                                           73/23.34
(Continued)

FOREIGN PATENT DOCUMENTS

CN    104750068 A    7/2015
JP      5582803 B2    9/2014
(Continued)

OTHER PUBLICATIONS

MSS alliance launched to set de facto standard for odor-sensing systems—aiming to establish basic elements of MSS technology towards practical use—[online], EC Corp., [viewed on Sep. 1, 2015], Internet <URL: http://ipn.nec.com/press/201509/20150929_01.html>, Sep. 29, 2015, 5 pages.
(Continued)

*Primary Examiner* — Jeong S Park
(74) *Attorney, Agent, or Firm* — Sughrue Mion, PLLC

(57) ABSTRACT

A server apparatus 10 is communicably connected to a terminal apparatus 20 that collects sensor data from an odor sensor 40. The server apparatus 10 includes an analyzer holding unit 11 that holds a plurality of analyzers for analyzing specific odor analysis targets, based on sensor data, an analyzer management unit 12 that selects an analyzer, determines preprocessing to be performed on the sensor data, according to the selected analyzer, and causes the terminal apparatus 20 to execute the preprocessing, an analysis execution unit 13 that executes analysis processing
(Continued)

of the designated odor analysis target, by applying the selected analyzer to the preprocessed sensor data from the terminal apparatus, and an analysis result transmission unit 14 that transmits information indicating a result of the analysis processing to the terminal apparatus 20.

17 Claims, 11 Drawing Sheets

(51) Int. Cl.
  *G01N 33/497* (2006.01)
  *G16Y 10/90* (2020.01)
  *G16Y 40/20* (2020.01)

(52) U.S. Cl.
  CPC ..... *G01N 33/4972* (2013.01); *H04L 67/2828* (2013.01); *H04L 67/2895* (2013.01); *G16Y 10/90* (2020.01); *G16Y 40/20* (2020.01)

(56) References Cited

U.S. PATENT DOCUMENTS

| | | | |
|---|---|---|---|
| 2016/0187279 A1* | 6/2016 | Tayebi | G01N 27/123 73/23.21 |
| 2017/0069010 A1* | 3/2017 | Amin | G06F 16/9537 |
| 2017/0173262 A1* | 6/2017 | Veltz | A61B 5/0022 |
| 2017/0199159 A1* | 7/2017 | Kuroki | G01N 33/0031 |
| 2019/0227053 A1* | 7/2019 | Rinberg | A61B 5/4011 |
| 2020/0111189 A1* | 4/2020 | Yeung | G06Q 10/06 |
| 2020/0300798 A1* | 9/2020 | Watanabe | G01N 33/0031 |
| 2020/0336543 A1* | 10/2020 | Watanabe | G06Q 50/10 |

FOREIGN PATENT DOCUMENTS

| | | |
|---|---|---|
| JP | 2017-067538 A | 4/2017 |
| JP | 6121014 B2 | 4/2017 |

OTHER PUBLICATIONS

Akio Sashima, et al., "Mobile-Sensing Platform: Consorts-S: Developing Healthcare Services by Using Cell Phones and Wireless Electrocardiograph Sensors", IPSJ SIG technical report, Jul. 19, 2007, pp. 23-28, vol. 2007, No. 74.

International Search Report for PCT/JP2018/036955 dated Dec. 25, 2018 [PCT/ISA/210].

Written Opinion for PCT/JP2018/036955 dated Dec. 25, 2018 [PCT/ISA/237].

International Preliminary Report on Patentability with translation of Written Opinion dated Apr. 16, 2020 from the International Bureau in International Application No. PCT/JP2018/036955.

\* cited by examiner

Fig.5

| ANALYZER ID | FEATURE AMOUNT EXTRACTION MODULE ID | ANALYSIS TARGET INFORMATION | ANALYSIS ACCURACY | INDEX LIST |
|---|---|---|---|---|
| ANALYZER 1 | MODULE 1 | A,B,C | 90% | i0,...i99 |
| ANALYZER 2 | MODULE 2 | A,B,C | 60% | j0,...j49 |
| ANALYZER 3 | MODULE 3 | C,D,E,F | 90% | k0,...k119 |
| ANALYZER 4 | MODULE 4 | C,D,E,F | 70% | h0,...h79 |
| ... | ... | ... | ... | ... |

SERVER APPARATUS, ODOR SENSOR DATA ANALYSIS METHOD, AND COMPUTER READABLE RECORDING MEDIUM FOR UNFIXED ODOR ANALYSIS TARGETS

CROSS REFERENCE TO RELATED APPLICATIONS

This application is a National Stage of International Application No. PCT/JP2018/036955 filed Oct. 2, 2018, claiming priority based on Japanese Patent Application No. 2017-193901 filed Oct. 3, 2017.

TECHNICAL FIELD

The present invention relates to a server apparatus and an odor sensor data analysis method that are for performing analysis of odor sensor data using an odor sensor capable of detecting a scent or an odor based on substances in the atmosphere, and, furthermore, relates to a computer-readable recording medium that includes a program recorded thereon for realizing the apparatus and method.

BACKGROUND ART

Heretofore, odor sensors have been used in order to detect specific odors (e.g., refer to Patent Documents 1 and 2). An odor sensor detects a specific odor, by detecting an airborne chemical substance that produces a specific odor with a sensor element. Also, a metal oxide and an organic semiconductor thin film are given as examples of a sensor element. With such a sensor element, conductivity changes when a specific chemical substance adheres thereto, thus enabling the specific chemical substance to be detected.

Incidentally, with conventional odor sensors, there is a problem in that detectable chemical substances are fixed, and thus the odors that are detected are also fixed, resulting in a lack of versatility. In response, a Membrane-type Surface stress Sensor (MSS) that is able to detect a wide range of substances has been newly proposed in recent years (refer to Non-Patent Document 1).

An MSS is usually constituted by two or more MSS elements. Each MSS element includes a circular portion provided with a sensitive membrane, a frame surrounding the circular portion, and a plurality of bridges for coupling the circular portion to the frame. A piezoresistive element is embedded in each bridge. In such a configuration, the circular portion deforms due to stress occurring in the sensitive membrane when a substance sticks to the sensitive membrane, resulting in stress being applied to the bridges. As a result, the electrical resistance of the piezoresistive elements embedded in the bridges changes greatly, thus enabling the substance stuck to the sensitive membrane to be detected from the resistance value.

Also, with an MSS, the material of the sensitive membrane differs for every MSS element, but this does not necessarily mean that the substance that sticks to each MSS element is fixed to one type. The material of the sensitive membrane of each MSS element is configured such that the pattern of the output data of the entire MSS that is obtained by compositing the output data of the respective MSS elements differs according to the odor, that is, the set of substances constituting the odor. Thus, with an MSS, it becomes possible to detect multiple types of odors, by learning output patterns and creating analyzers, for every odor that serves as an analysis target, though machine learning in advance.

Note that there is also a technique that involves using a plurality of odor sensors having different characteristics including odor sensors other than an MSS, performing analysis through machine learning by combining data from the respective odor sensors, and generating an odor analyzer for every target.

Also, with such odor sensors, application of edge computing, which has attracted attention in the IoT (Internet of Things) field in recent years, is effective. The reasons for this are as follows.

First, in edge computing, sensor data can be collected with a small-scale computer system called an edge that is disposed comparatively close to the plurality of sensors. Also, the edge can be made to perform preprocessing that includes data amount reduction processing and feature amount extraction processing on collected sensor data, and a cloud can be made to perform analysis processing that uses analyzers. Accordingly, in the case where edge computing is applied to odor sensors, processing can be distributed and sensor data can be efficiently processed.

LIST OF RELATED ART DOCUMENTS

Patent Document

Patent Document 1: Japanese Patent No. 6121014
Patent Document 2: Japanese Patent No. 5582803

Non-Patent Document

Non-Patent Document 1: MSS alliance launched to set de facto standard for odor-sensing systems—aiming to establish basic elements of MSS technology towards practical use—[online], Sep. 29, 2015, NEC Corp., [viewed on Sep. 1, 2015], Internet <URL: http://jpn.nec.com/press/201509/20150929_01.html>

SUMMARY OF INVENTION

Problems to be Solved by the Invention

Incidentally, as described above, in edge computing, the edge performs analysis of sensor data by performing preprocessing such as data amount reduction and feature amount extraction on collected sensor data, but the contents of the preprocessing also differs for every analysis target, when the analyzer is changed for every analysis target as described above. In other words, in the case of using sensor data, the range and type of sensor data to be reduced and the feature amount to be extracted also change every time the analysis target changes. Thus, freely changing the analysis target during operation is difficult to achieve simply by applying conventional edge computing to odor sensors.

On the other hand, it is conceivable that such problems can be resolved if the edge is configured to transmit all collected sensor data to a cloud. However, in the case where a plurality of odor sensors with different characteristics are combined as in the case of an MSS, data is output for every sensor element, and thus, for example, if the sampling rate is 100 Hz and the number of sensor elements is four, even 20 seconds of measurement will result in 8000 pieces of data. In this case, the communication line will be put under pressure, together with increasing the processing load on the cloud.

An example object of the invention is to provide a server apparatus, an odor sensor data analysis method and a computer-readable recording medium that, in the case where edge computing is applied to an odor sensor whose odor analysis target is not fixed, can enable analysis of analysis targets, without increasing the load on the system.

Means for Solving the Problems

A server apparatus according to an example aspect of the invention is configured to be communicably connected to a terminal apparatus for collecting sensor data from an odor sensor that outputs the sensor data in reaction to a plurality of types of odors, the server apparatus including:

an analyzer holding unit configured to hold a plurality of analyzers for analyzing specific odor analysis targets, based on the sensor data;

an analyzer management unit configured to select an analyzer capable of analyzing a designated odor analysis target, from among the plurality of analyzers, determine preprocessing to be performed on the sensor data, according to the selected analyzer, and cause the terminal apparatus to execute the determined preprocessing on the sensor data;

an analysis execution unit configured to, upon the preprocessed sensor data being transmitted thereto from the terminal apparatus, execute analysis processing of the designated odor analysis target, by applying the selected analyzer to the preprocessed sensor data transmitted thereto; and an analysis result transmission unit configured to transmit information indicating a result of the analysis processing to the terminal apparatus.

A terminal apparatus according to an example aspect of the invention is for collecting sensor data from an odor sensor that outputs the sensor data in reaction to a plurality of types of odors and configured to be communicably connected to a server apparatus that holds a plurality of analyzers for analyzing specific odor analysis targets, based on the sensor data, the terminal apparatus including:

a sensor data collection unit configured to collect the sensor data;

a preprocessing unit configured to, in a case where, in the server apparatus, an analyzer capable of analyzing a designated odor analysis target is selected, from among the plurality of analyzer, and preprocessing to be performed on the sensor data is determined, according to the selected analyzer, execute the determined preprocessing on the collected sensor data;

a sensor data transmission unit configured to transmit the preprocessed sensor data to the server apparatus; and an analysis result holding unit configured to, in a case where, in the server apparatus, analysis processing of the designated analysis target is executed, by the selected analyzer being applied to the preprocessed sensor data transmitted thereto, hold information indicating a result of the analysis processing.

Also, an odor sensor data analysis method according to an example aspect of the invention uses a terminal apparatus for collecting sensor data from an odor sensor that outputs the sensor data in reaction to a plurality of types of odors and a server apparatus configured to be communicably connected to the terminal apparatus, the method comprising:

(a) a step of, with the terminal apparatus, collecting the sensor data;

(b) a step of, with the server apparatus, selecting an analyzer capable of analyzing a designated odor analysis target, from among a plurality of analyzers for analyzing specific odor analysis targets by analyzing the sensor data, and determining preprocessing to be performed on the sensor data, according to the selected analyzer;

(c) a step of, with the terminal apparatus, executing the determined preprocessing on the sensor data;

(d) a step of, with the terminal apparatus, transmitting the preprocessed sensor data to the server apparatus;

(e) a step of, with the server apparatus, executing analysis processing of the designated odor analysis target, by applying the selected analyzer to the preprocessed sensor data transmitted thereto from the terminal apparatus;

(f) a step of, with the server apparatus, transmitting information indicating a result of the analysis processing to the terminal apparatus; and (g) a step of, with the terminal apparatus, holding the information indicating the result of the analysis processing.

Furthermore, a computer-readable recording medium according to an example aspect of the invention includes a program recorded thereon, the program including instructions that cause a computer configured to be communicably connected to a terminal apparatus for collecting sensor data from an odor sensor that outputs the sensor data in reaction to a plurality of types of odors to carry out:

(a) a step of holding a plurality of analyzers for analyzing specific odor analysis targets, based on the sensor data;

(b) a step of selecting an analyzer capable of analyzing a designated odor analysis target, from among the plurality of analyzers, determining preprocessing to be performed on the sensor data, according to the selected analyzer, and causing the terminal apparatus to execute the determined preprocessing on the sensor data;

(c) a step of, upon the preprocessed sensor data being transmitted thereto from the terminal apparatus, executing analysis processing of the designated odor analysis target, by applying the selected analyzer to the preprocessed sensor data transmitted thereto; and (d) a step of transmitting information indicating a result of the analysis processing to the terminal apparatus.

Furthermore, a computer-readable recording medium according to an example aspect of the invention includes a program recorded thereon, the program including instructions that cause a computer for collecting sensor data from an odor sensor that outputs the sensor data in reaction to a plurality of types of odors and configured to be communicably connected to a server apparatus that holds a plurality of analyzers for analyzing specific odor analysis targets based on the sensor data to carry out:

(a) a step of collecting the sensor data;

(b) a step of, in a case where, in the server apparatus, an analyzer capable of analyzing a designated odor analysis target is selected, from among the plurality of analyzers, and preprocessing to be performed on the sensor data is determined, according to the selected analyzer, executing the determined preprocessing on the collected sensor data;

(c) a step of transmitting the preprocessed sensor data to the server apparatus; and (d) a step of, in a case where, in the server apparatus, analysis processing of the designated analysis target is executed, by the selected analyzer being applied to the preprocessed sensor data transmitted thereto, holding information indicating a result of the analysis processing.

Advantageous Effects of the Invention

As described above, according to the invention, in the case where edge computing is applied to an odor sensor whose odor analysis target is not fixed, it becomes possible to analyze analysis targets, without increasing the load on the system.

BRIEF DESCRIPTION OF THE DRAWINGS

FIG. 5 is a diagram showing an example of a table that is used in selection of an analyzer and determination of preprocessing in the example embodiment of the invention.

EXAMPLE EMBODIMENTS

Example Embodiment

Hereinafter, a server apparatus, a terminal apparatus, an odor sensor data analysis method and a program according to an example embodiment of the invention will be described, with reference to FIGS. 1 to 11.

[Apparatus Configuration]

Figure 1:
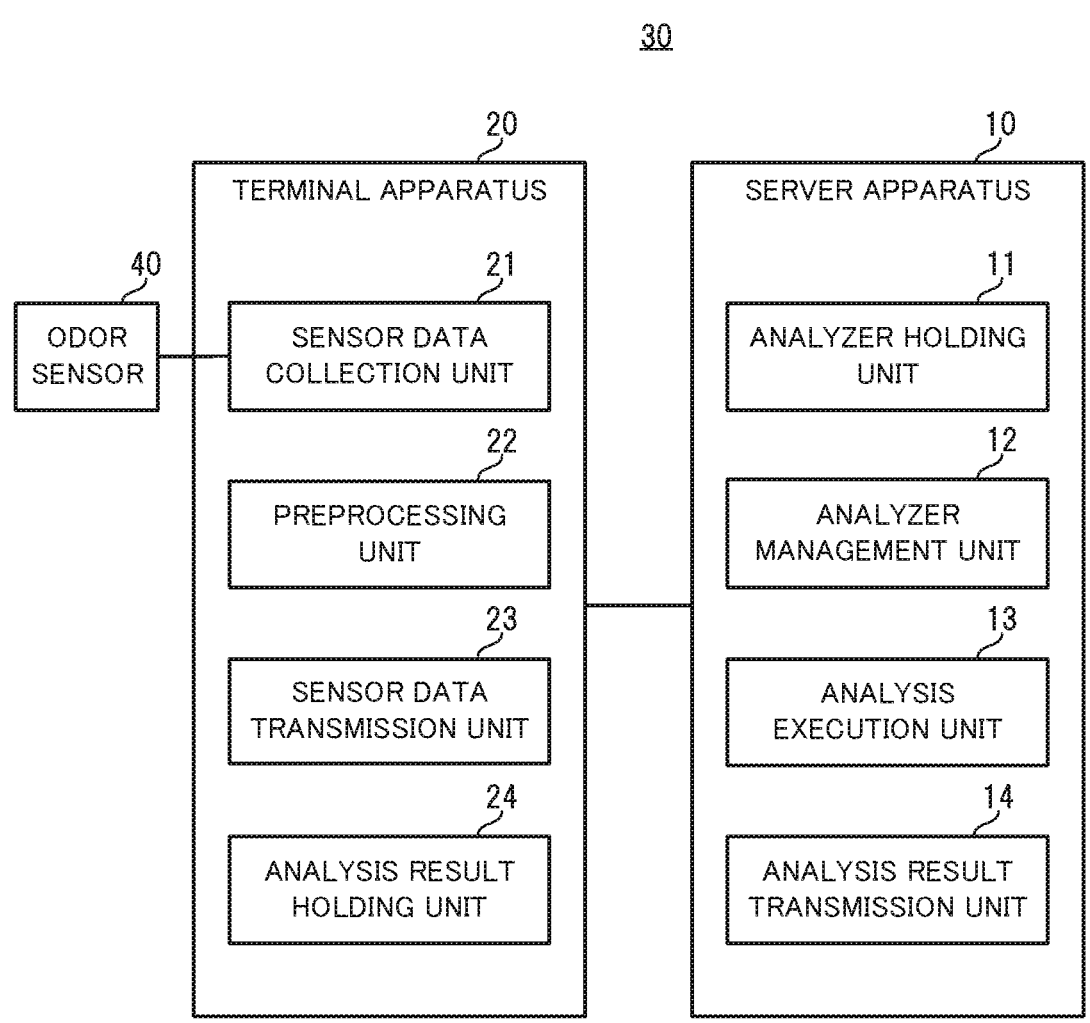
FIG. 1 is a block diagram showing schematic configurations of a server apparatus and a terminal apparatus according to an example embodiment of the invention.

Initially, schematic configurations of the server apparatus and the terminal apparatus according to the example embodiment will be described. FIG. 1 is a block diagram showing schematic configurations of the server apparatus and the terminal apparatus according to the example embodiment of the invention.

A server apparatus 10 and a terminal apparatus 20 shown in FIG. 1 constitute a system 30 for analyzing odors using an odor sensor 40. The odor sensor 40 that is used in the example embodiment is a sensor that outputs sensor data in reaction to a plurality of types of odors. Also, with the odor sensor 40, it becomes possible to analyze various odor analysis targets, by using a number of analyzers that analyze specific odor analysis targets, based on sensor data.

In the example embodiment, "odor" includes not only scents and smells that people experience with their sense of smell but also gas molecules that are produced from the expiration or excretion of organisms and chemical composition elements (gas molecules, etc.) included in the outside air that reflect the situation of the target whose analysis is sought, such as the illness of an organism or the degradation of a structure.

Also, "odor analysis targets" include the actual odors that serve as an analysis target, and, furthermore, the contraction of diseases that produces odors, the degree of ripeness of fruit that likewise produces odors, the degree of degradation of structures that likewise produces odors.

As shown in FIG. 1, the server apparatus 10 and the terminal apparatus 20 are communicably connected to each other. The terminal apparatus 20 collects sensor data (henceforth, also referred to as "odor sensor data") from the odor sensor 40. The server apparatus 10 executes analysis processing on a designated odor analysis target, based on the sensor data collected by the terminal apparatus 20.

Also, as shown in FIG. 1, the server apparatus 10 includes an analyzer holding unit 11, an analyzer management unit 12, an analysis execution unit 13, and an analysis result transmission unit 14. Of these, the analyzer holding unit 11 holds a plurality of analysis devices for analyzing specific odor analysis targets by analyzing sensor data.

The analyzer management unit 12 selects an analyzer capable of analyzing a designated odor analysis target, from among the plurality of analyzers. Also, the analyzer management unit 12 determines preprocessing to be performed on the sensor data, according to the selected analyzer, and causes the terminal apparatus 20 to execute the determined preprocessing on the sensor data.

The analysis execution unit 13, upon preprocessed sensor data being transmitted thereto from the terminal apparatus 20, executes analysis processing of the designated odor analysis target, by applying the selected analyzer to the preprocessed sensor data transmitted thereto. The analysis result transmission unit 14 transmits information indicating a result of the analysis processing by the analysis execution unit 13 to the terminal apparatus 20.

Also, as shown in FIG. 1, the terminal apparatus 20 includes a sensor data collection unit 21, a preprocessing unit 22, a sensor data transmission unit 23, and an analysis result holding unit 24. Of these, the sensor data collection unit 21 collects sensor data.

The preprocessing unit 22, in the case where, in the server apparatus 10, an analyzer capable of analyzing the designated odor analysis target is selected, from among the plurality of analyzers, and, furthermore, preprocessing to be performed on the sensor data is determined, according to the selected analyzer, executes the determined preprocessing on the collected sensor data.

The sensor data transmission unit 23 transmits the preprocessed sensor data to the server apparatus 10. The analysis result holding unit 24, in the case where, in the server apparatus 10, analysis processing of the designated odor analysis target is executed, by the selected analyzer being applied to the preprocessed sensor data transmitted thereto, receives and holds information indicating the result of the analysis processing.

In this way, in the example embodiment, the odor sensor 40 is utilized by edge computing that includes the server apparatus 10 and the terminal apparatus 20. With the server apparatus 10, an appropriate analyzer is selected, according to the odor analysis target, thus enabling analysis of various types of odors by the odor sensor 40. Also, since the terminal apparatus 20 executes preprocessing on sensor data, according to the analyzer to be used, that is, according to the odor analysis target, only required data is transmitted to the server apparatus 10.

Thus, according to the example embodiment, in the case where edge computing is applied to an odor sensor whose odor analysis target is not fixed, it becomes possible to analyze odor analysis targets, without increasing the load on the system.

Also, in the example embodiment, not only can the actual gas molecules that produce odors be detected but prediction of the contraction of diseases, prediction of the degree of degradation of structures and the like can also be performed as analysis processing. It becomes possible to execute such analysis processing through performing machine learning, by providing the results of such prediction as training data for machine learning for when building analyzers. In this case, whether or not a disease has been contracted can be analyzed from the expiration of an organism, or the degree of degradation of a structure can be analyzed from the air within a building. In the example embodiment, an "analysis target" refers to the result that is sought through analysis. In the above example, the contraction of a disease and the degree of degradation of a structure correspond to analysis targets.

Figure 2:
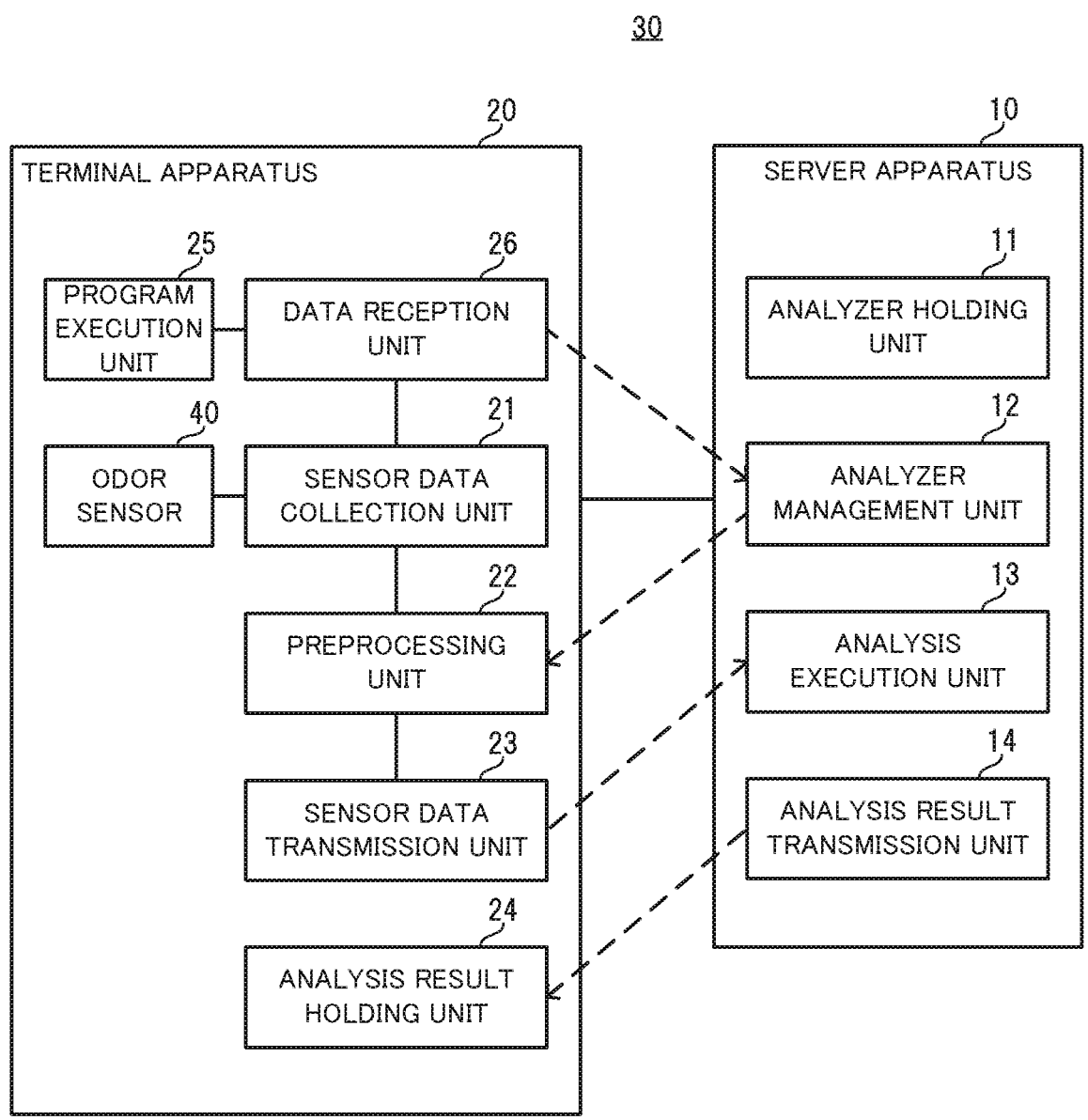
FIG. 2 is a block diagram more specifically showing the configurations of the server apparatus and the terminal apparatus according to the example embodiment of the invention.
Figure 3:
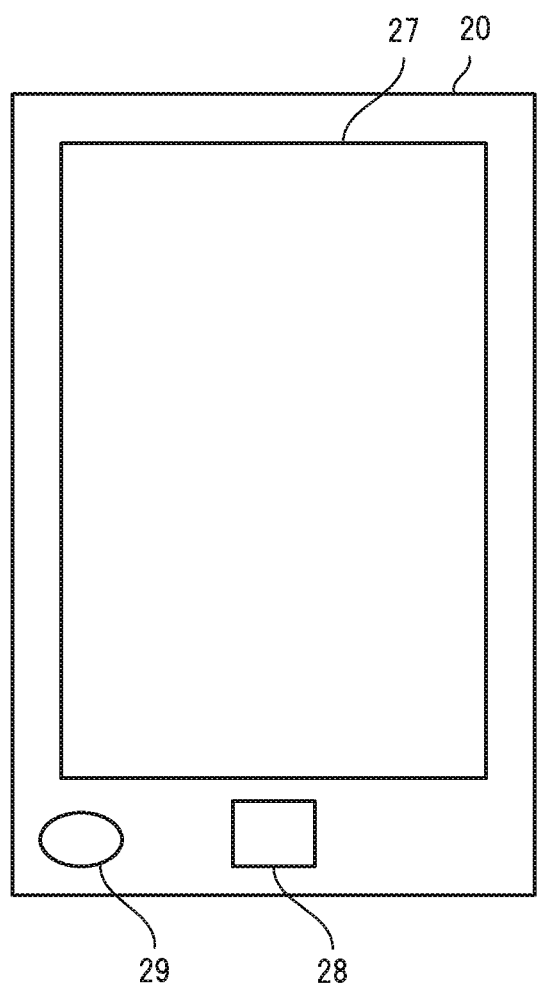
FIG. 3 is a diagram showing an external appearance of the terminal apparatus according to the example embodiment of the invention.
Figure 4:
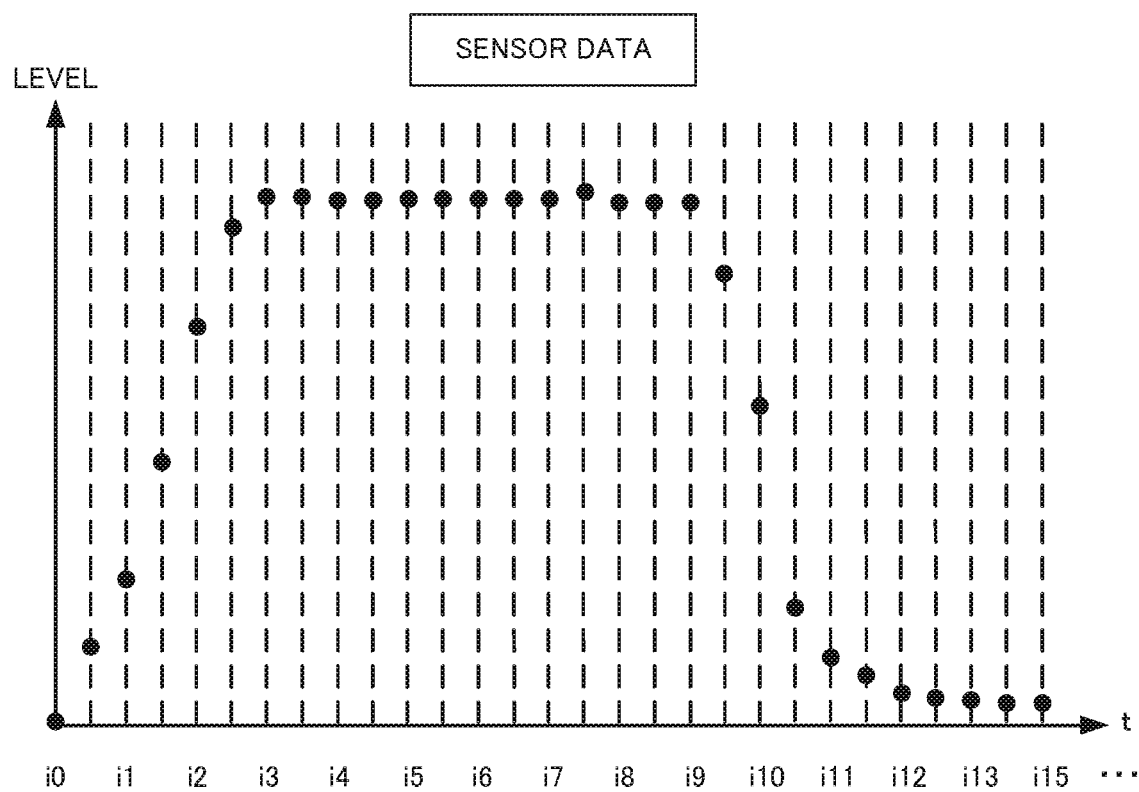
FIG. 4 is a diagram showing an example of sensor data that is output by an odor sensor in the example embodiment of the invention.
Figure 6A:
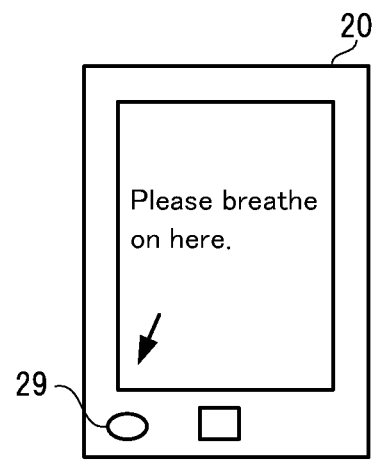
FIGS. 6A, 6B, and 6C show an example of information that is displayed on a screen of the terminal apparatus.
Figure 6B:
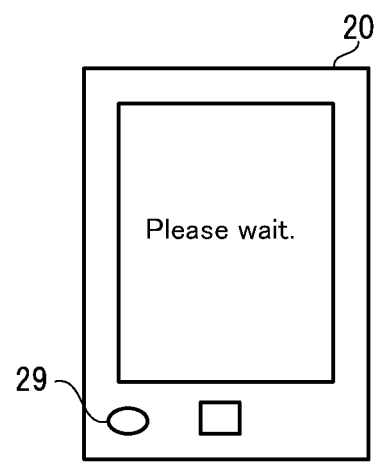
Figure 6C:
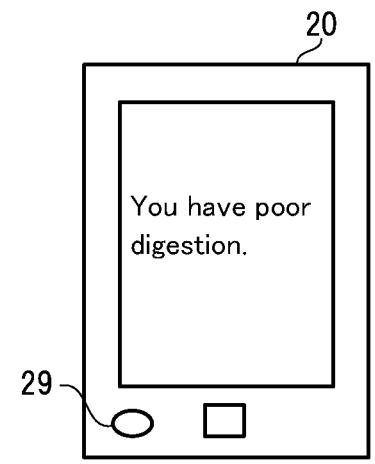

Next, the configurations of the server apparatus 10 and the terminal apparatus 20 according to the example embodiment will be more specifically described, using FIGS. 2 to 5. FIG. 2 is a block diagram more specifically showing the configurations of the server apparatus and the terminal apparatus according to the example embodiment of the invention. FIG. 3 is a diagram showing an external appearance of the terminal apparatus according to the example embodiment of the invention. FIG. 4 is a diagram showing an example of sensor data that is output by the odor sensor in the example embodiment of the invention. FIG. 5 is a diagram showing an example of a table that is used in selection of an analyzer and determination of preprocessing in the example embodiment of the invention. FIGS. 6A, 6B, and 6C show an example of information that is displayed on the screen of the terminal apparatus.

First, the terminal apparatus 20 will be specifically described. As shown in FIG. 2, in the example embodiment, the terminal apparatus 20 further includes a program execution unit 25 and a data reception unit 26, in addition to the sensor data collection unit 21, the preprocessing unit 22, the sensor data transmission unit 23, and the analysis result holding unit 24.

The program execution unit 25 executes an application program that has been imported to the terminal apparatus 20. A program that performs processing according to odor sensor data analysis results obtained through odor sensor data sensed by the odor sensor 40 being analyzed by the terminal apparatus 20 and the server apparatus 10 is given as an example of an application program. Specifically, examples of an application program include a program that analyzes alcohol contained in the breath of a user of the terminal apparatus 20, a program that analyzes odors contained in the body odor of a user of the terminal apparatus 20, and a program that analyzes the degree of ripeness of fruit from the odor of the fruit.

Also, in the example embodiment, the application program designates one or more odor analysis targets. Furthermore, the application program also designates the accuracy at which to analyze the designated one or more odor analysis targets.

The data reception unit 26 receives the designations, by the application program that operates on the terminal apparatus 20, of the one or more odor analysis targets and the accuracy at which to analyze the designated one or more odor analysis targets. The data reception unit 26 notifies the designated one or more odor analysis targets and the designated accuracy to the server apparatus 10.

Also, the data reception unit 26 includes a general-purpose application program interface (API). The data reception unit 26 is also able to receive designations other than from an application program described in the example embodiment, such as information on a designated odor from another apparatus via a network, for example. Information that the data reception unit 26 is capable of receiving may be information relating to alcohol or body odor, information on the contraction of a disease by an organism, information on the degree of ripeness of fruit, information on the degree of degradation of a structure or the like sought as an analysis result, other than the gas molecules constituting the actual odor. Based on this analysis target information, the data reception unit 26 specifies an appropriate analyzer from among analyzers registered in advance.

Also, in the example embodiment, the terminal apparatus 20 is constituted by a terminal apparatus (hereinafter, referred to as a "communication terminal") provided with a communication function such as a smartphone, and, furthermore, internally includes the odor sensor 40. Thus, as shown in FIG. 3, the terminal apparatus 20 includes a display device 27. Furthermore, a window 29 for guiding the odor that serves as an analysis target to the odor sensor 40 is provided in the casing of the terminal apparatus 20. Also, in FIG. 3, reference numeral 28 denotes an operation button of the terminal apparatus 20.

Also, in the example embodiment, the abovementioned MSS is used as the odor sensor 40, for example. In this case, the sensor data output by the odor sensor 40 will be as shown in FIG. 4. In the example in FIG. 4, sensor data output by one of the MSS elements constituting the MSS is shown. Also, the odor sensor 40 outputs sensor data at a set sampling rate. Note that i0, i1, i2 and so on that are shown in FIG. 4 are indexes, a description of which will be given later. Also, in the indexes, "i" indicates output from a specific MSS element. In the case of output from a different MSS element, a letter other than "i" is allocated.

Next, the server apparatus 10 will be specifically described. First, in the example embodiment, each analyzer that is being held by the analyzer holding unit 11 is an analysis model created in advance by machine learning. Analysis models are created by machine learning the features of sensor data, with a support vector machine, using sensor data output by the odor sensor 40 when there is a reaction to test odors as learning data, and using data specifying test odors as training data, for example.

Also, in the example embodiment, machine learning is performed utilizing the sparsity of sensor data, for example. In other words, the chemical behavior of an odor that serves as an analysis target and sensor elements and the physical characteristics of the odor sensor 40 are aggregated and appear in specific portions within the sensor data. In the example in FIG. 4, such behavior and characteristics appear in the rising portion of sensor data, the flat upper portion of the waveform, and the like. Accordingly, an appropriate analysis model can be built, even with machine learning that uses only a specific portion of the sensor data. Furthermore, the analysis accuracy can also be determined by the amount of data that is used in machine learning.

Thus, in the example embodiment, machine learning may be performed by extracting only an effective portion of sensor data serving as learning data. By using a technology called feature selection, for example, the portion effective for learning and analysis can be specified and extracted from sensor data serving as learning data. Also, the portion that is extracted at this time is specified by the indexes shown in FIG. 4, and the specified indexes are utilized in preprocessing discussed later.

The analyzer management unit 12, in the example embodiment, selects, from among the plurality of analyzers, an analyzer capable of analyzing a designated odor analysis target and capable of achieving the designated accuracy, because of accuracy also be designated as described above.

Also, the analyzer management unit 12, in the example embodiment, specifies a feature amount to be extracted from sensor data, according to the selected analyzer. The analyzer management unit 12 then determines processing for extracting the specified feature amount as preprocessing, and transmits a program module (hereinafter, referred to as a "feature amount extraction module") for executing the determined preprocessing to the terminal apparatus 20.

Specifically, the analyzer management unit 12 performs selection of an analyzer and determination of corresponding preprocessing (feature amount extraction module), using the table shown in FIG. 5. As shown in FIG. 5, a corresponding feature amount extraction module, analysis target information, analysis accuracy and an index list are registered for every analyzer on respective lines of the table. The analysis target information is information sought as an analysis result, with gas molecules constituting the actual odor that serves as an analysis target, breath alcohol concentration, the degree of ripeness of fruit and contraction of a specific disease being given as specific examples. Also, in this table, the index list on each line indicates sensor data used in learning by the corresponding analyzer, and also indicates the feature amount that is extracted with the feature amount extraction module on the same line.

For example, supposing an analyzer 1 is selected, a feature amount extraction module 1 will be transmitted to the terminal apparatus 20. Accordingly, in the terminal apparatus 20, the preprocessing unit 22 executes the feature amount extraction module 1, and, as preprocessing, extracts data corresponding to i0, . . . i99 in the index list from the sensor data as a feature amount.

In this way, in the example embodiment, since thinning of sensor data is performed by preprocessing, the load on the system is eased. Also, analysis of an odor becomes possible, because thinning of sensor data is performed in conformance with an analyzer selected according to the odor analysis target.

In the example embodiment, the analysis execution unit 13 is also able to analyze the level of the analyzed odor analysis target from the result of the analysis processing. As a specific example, the analysis execution unit 13 estimates the graded level of an odor, according to the concentration of analyzed odor molecules. Also, in this case, the analysis result transmission unit 14 transmits information indicating the estimated level of the odor to the terminal apparatus 20, as information indicating the result of the analysis processing.

In the terminal apparatus 20, the analysis result holding unit 24 is thereby able to display the estimated level of the odor on the screen of the display device 27. Also, in the example embodiment, the terminal apparatus 20 is able to display information supporting operations by the user on the screen of the display device 27, as shown in FIGS. 6A, 6B, and 6C.

[Apparatus Operations]

Next, operations of the server apparatus 10 and the terminal apparatus 20 according to the example embodiment will be described using FIGS. 7 and 8. Also, in the following description, FIGS. 1 to 6 will be referred to as appropriate.

Furthermore, in the example embodiment, the odor sensor data analysis method is implemented, by operating the server apparatus 10 and the terminal apparatus 20. Therefore, the following description of the operations of the server apparatus 10 and the terminal apparatus 20 will be given in place of a description of the odor data analysis method according to the example embodiment.

Figure 7:
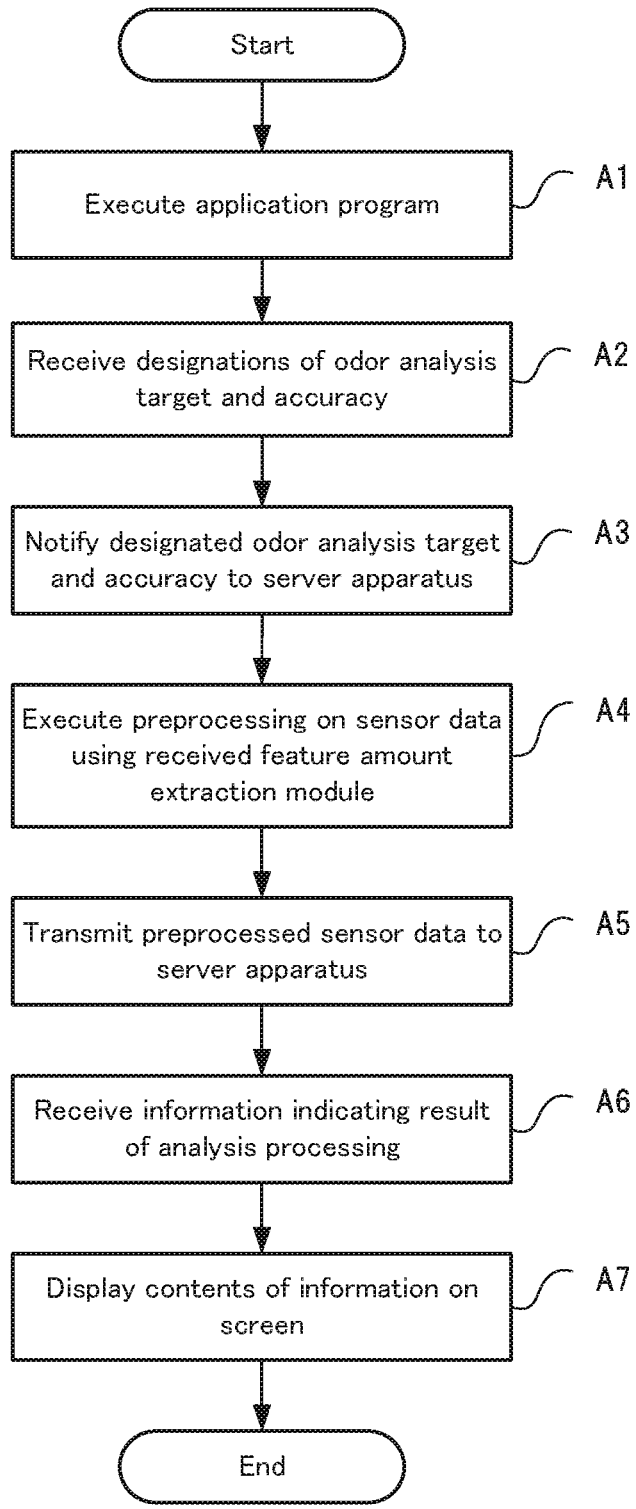
FIG. 7 is a flowchart showing operations of the terminal apparatus according to the example embodiment of the invention.

First, operations of the terminal apparatus 20 will be specifically described using FIG. 7. FIG. 7 is a flowchart showing operations of the terminal apparatus according to the example embodiment of the invention.

Initially, as shown in FIG. 7, in the terminal apparatus 20, the program execution unit 25 executes the application program (step A1).

Next, the application program designates one or more odor analysis targets and the accuracy at which to analyze the designated one or more odor analysis target, and inputs the designated one or more odor analysis targets and the accuracy to the data reception unit 26. The data reception unit 26 receives the designations of the one or more odor analysis targets and the accuracy (step A2). Then, the data reception unit 26 notifies the designated one or more odor analysis targets and the designated accuracy to the server apparatus 10 (step A3).

Upon step A3 being executed, in the server apparatus 10, steps B1 to B4 are executed, in FIG. 8 described later. The terminal apparatus 20 thereby receives a feature amount extraction module, and the preprocessing unit 22 executes preprocessing, using the feature amount extraction module 1 (step A4). Feature amounts are thereby extracted from sensor data.

Next, the sensor data transmission unit 23 transmits sensor data that has undergone preprocessing in step A4, that is, the extracted feature amount, to the server apparatus 10 (step A5).

Upon step A5 being executed, in the server apparatus 10, steps B5 to B7 are executed, in FIG. 8 described later. The analysis result holding unit 24 thereby receives information indicating the result of the analysis processing from the server apparatus 10 (step A6). The analysis result holding unit 24 then displays the contents of the received information on the screen of the display device 27 (step A7).

Figure 8:
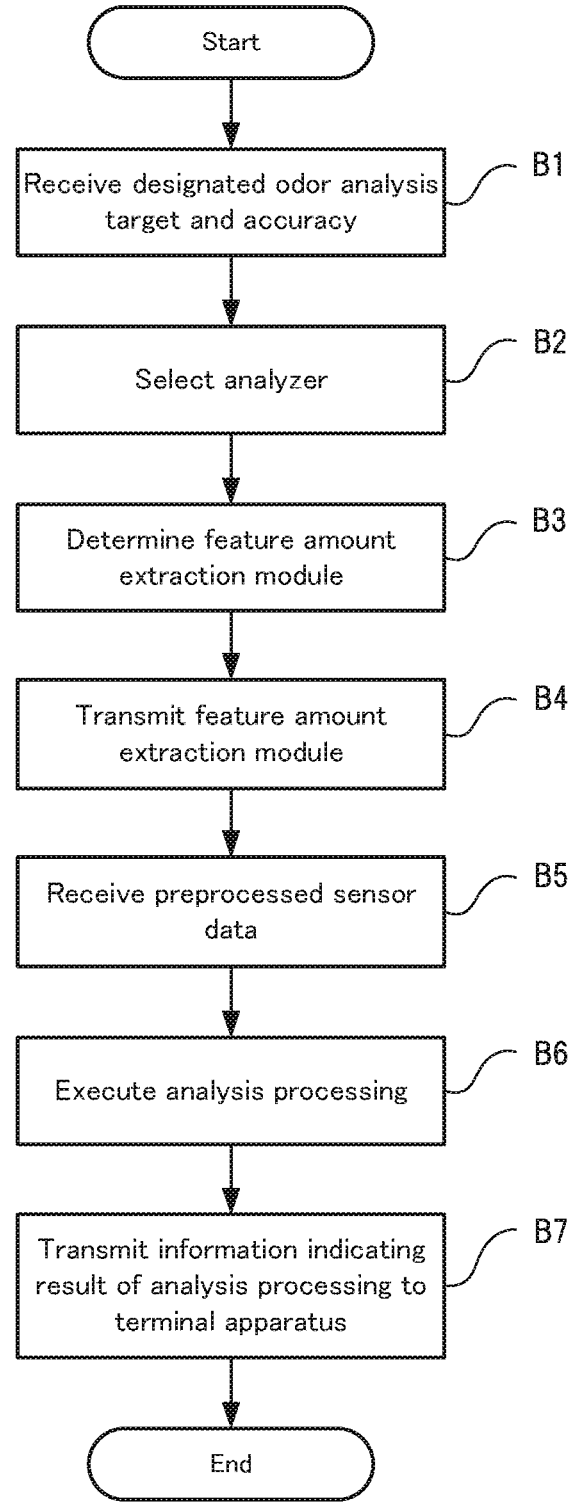
FIG. 8 is a flowchart showing operations of the server apparatus according to the example embodiment of the invention.

Next, operations of the server apparatus 10 will be specifically described using FIG. 8. FIG. 8 is a flowchart showing operations of the server apparatus according to the example embodiment of the invention.

Upon steps A1 to A3 shown in FIG. 7 being executed, the server apparatus 10, as shown in FIG. 8, receives the one or more odor analysis targets and the accuracy designated in step A2 (step B1).

Next, the analyzer management unit 12 selects an analyzer capable of analyzing the designated odor analysis target and capable of achieving the designated accuracy, from among the analyzers that are being held in the analyzer holding unit 11 (step B2).

Next, the analyzer management unit 12 determines a feature amount extraction module corresponding to the analyzer selected in step B2 (step B3), and transmits the determined feature amount extraction module to the terminal apparatus 20 (step B4).

Specifically, in steps B2 to B4, the analyzer management unit 12, first, collates the designated odor analysis target with the analysis target information and selects matching lines from the table shown in FIG. 5. Next, the analyzer management unit 12 specifies lines in which the analysis accuracy matches the designated accuracy, from among the selected lines.

Furthermore, the analyzer management unit 12 specifies a line in which the size of the index list is smallest, from among the specified lines. The analyzer management unit 12 then selects an analyzer and a feature amount extraction module that correspond to this line that was specified last, and transmits the selected feature amount extraction module to the terminal apparatus 40.

After execution of step B4, steps A4 and A5 are executed in the terminal apparatus 20. Next, the server apparatus 10 receives the preprocessed sensor data transmitted thereto from the terminal apparatus 20 (step B5).

Next, the analysis execution unit 13 executes analysis processing of the designated odor analysis target, by applying the analyzer selected in step B2 to the preprocessed sensor data that is received (step B6). Thereafter, the analysis result transmission unit 14 transmits information indicating the result of the analysis processing in step B6 to the terminal apparatus 20. Then, in the terminal apparatus 20, steps A6 and A7 are executed.

[Effect of Example Embodiment]

As described above, according to the example embodiment, in the server apparatus 10, the appropriate analyzer and feature amount extraction module are selected, and, according to these selections, the terminal apparatus 20 executes preprocessing, and extraction of a feature amount from sensor data is performed. As a result, only minimum data is communicated between the server apparatus 10 and the terminal apparatus 20, and analysis of the designated odor sensor data is also appropriately performed.

[Variations]

Figure 9:
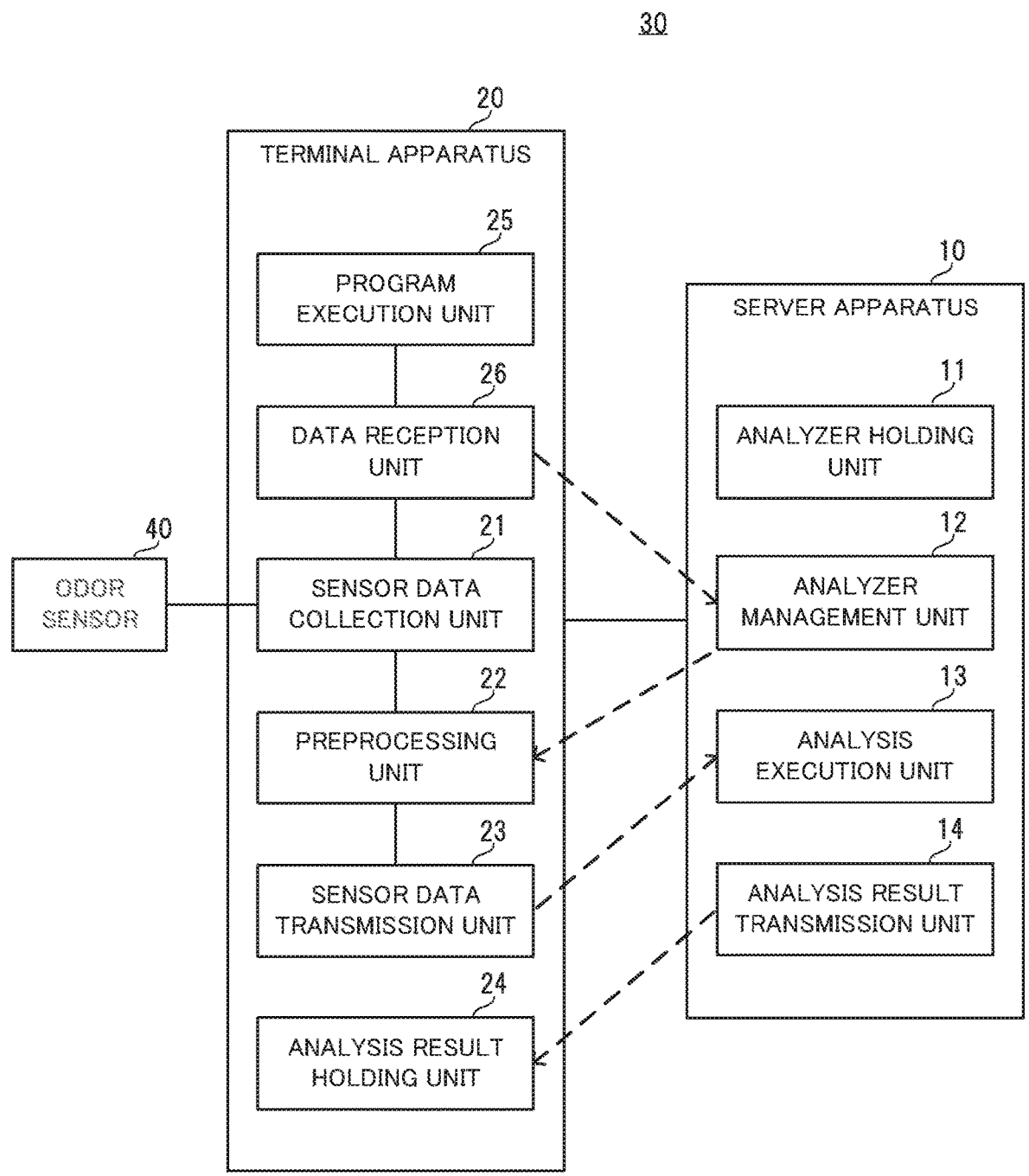
FIG. 9 is a block diagram showing configurations of the server apparatus and a variation of the terminal apparatus according to the example embodiment of the invention.
Figure 10:
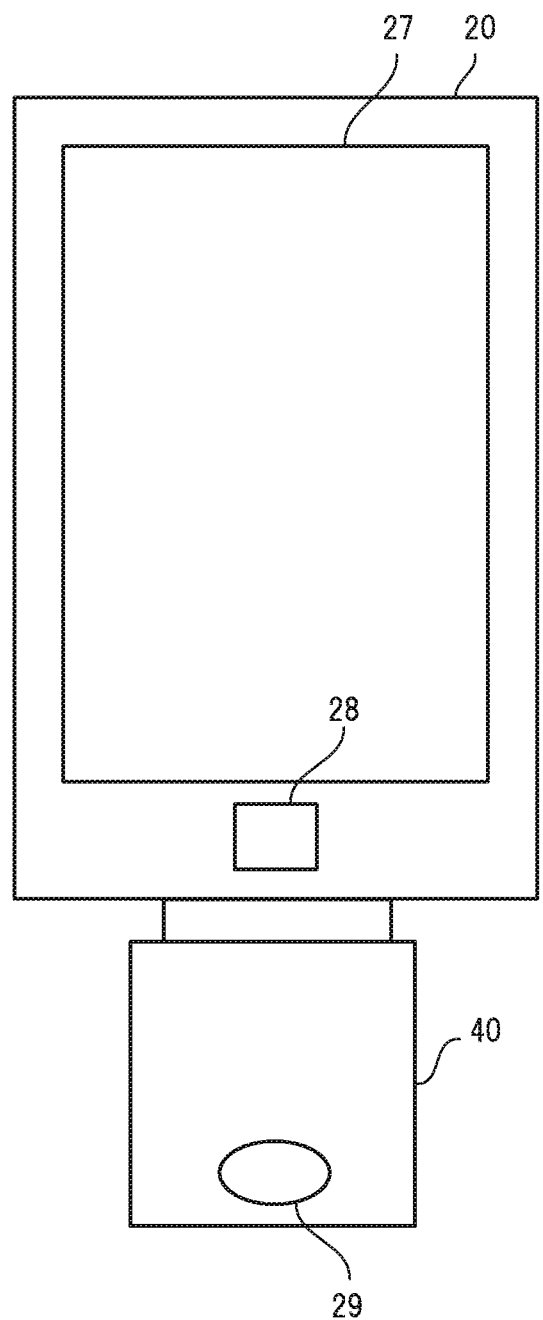
FIG. 10 is a diagram showing an external appearance of the variation of the terminal apparatus according to the example embodiment of the invention.

In the example shown in FIGS. 1 and 2, the terminal apparatus 20 is constituted by a communication terminal, and internally includes the odor sensor 40, although, in the example embodiment, the terminal apparatus 20 is not limited to this configuration. Here, a variation of the terminal apparatus 20 according to the example embodiment will be described, using FIGS. 9 and 10. FIG. 9 is a block diagram showing configurations of the server apparatus and the variation of the terminal apparatus according to the example embodiment of the invention. FIG. 10 is a diagram showing an external appearance of the variation of the terminal apparatus according to the example embodiment of the invention.

As shown in FIG. 9, in this variation, the odor sensor 40 is provided outside the terminal apparatus 20. Also, as shown in FIG. 10, the odor sensor 40 is connected to the terminal apparatus 20, via an interface for external connection of the terminal apparatus 20, which is a communication terminal.

According to this variation, detection of substances in the atmosphere can be executed, by connecting the odor sensor 40 to a general-purpose communication terminal. Also, odor sensor 40 is directly connected to the terminal apparatus 20 in this variation, but the connection therebetween need only be implemented in a manner that enables communication, and may be implemented wirelessly or by cable.

[Program 1]

A first program according to the example embodiment need only be a program that causes a computer to execute steps A1 to A7 shown in FIG. 7. The terminal apparatus 20 according to the example embodiment can be realized, by installing this program on a computer and executing the installed program. In this case, a processor of the computer performs processing while functioning as the sensor data collection unit 21, the preprocessing unit 22, the sensor data transmission unit 23, the analysis result holding unit 24, the program execution unit 25, and the data reception unit 26.

Also, a computer mounted in a communication terminal and a general-purpose computer are given as examples of the computer.

Also, the first program according to the example embodiment may be executed by a computer system built from a plurality of computers. In this case, for example, the computers may respectively function as one of the sensor data collection unit 21, the preprocessing unit 22, the sensor data transmission unit 23, the analysis result holding unit 24, the program execution unit 25, and the data reception unit 26.

[Program 2]

A second program according to the example embodiment need only be a program that causes a computer to execute steps B1 to B7 shown in FIG. 8. The server apparatus 10 according to the example embodiment can be realized, by installing this program on a computer and executing the installed program. In this case, a processor of the computer performs processing while functioning as the analyzer holding unit 11, the analyzer management unit 12, the analysis execution unit 13, and the analysis result transmission unit 14. Also, a general-purpose computer and a server computer are given as examples of the computer.

The second program according to the example embodiment may also be executed by a computer system built from a plurality of computers. In this case, for example, the computers may respectively function as one of the analyzer holding unit 11, the analyzer management unit 12, the analysis execution unit 13, and the analysis result transmission unit 14.

[Physical Configuration]

Figure 11:
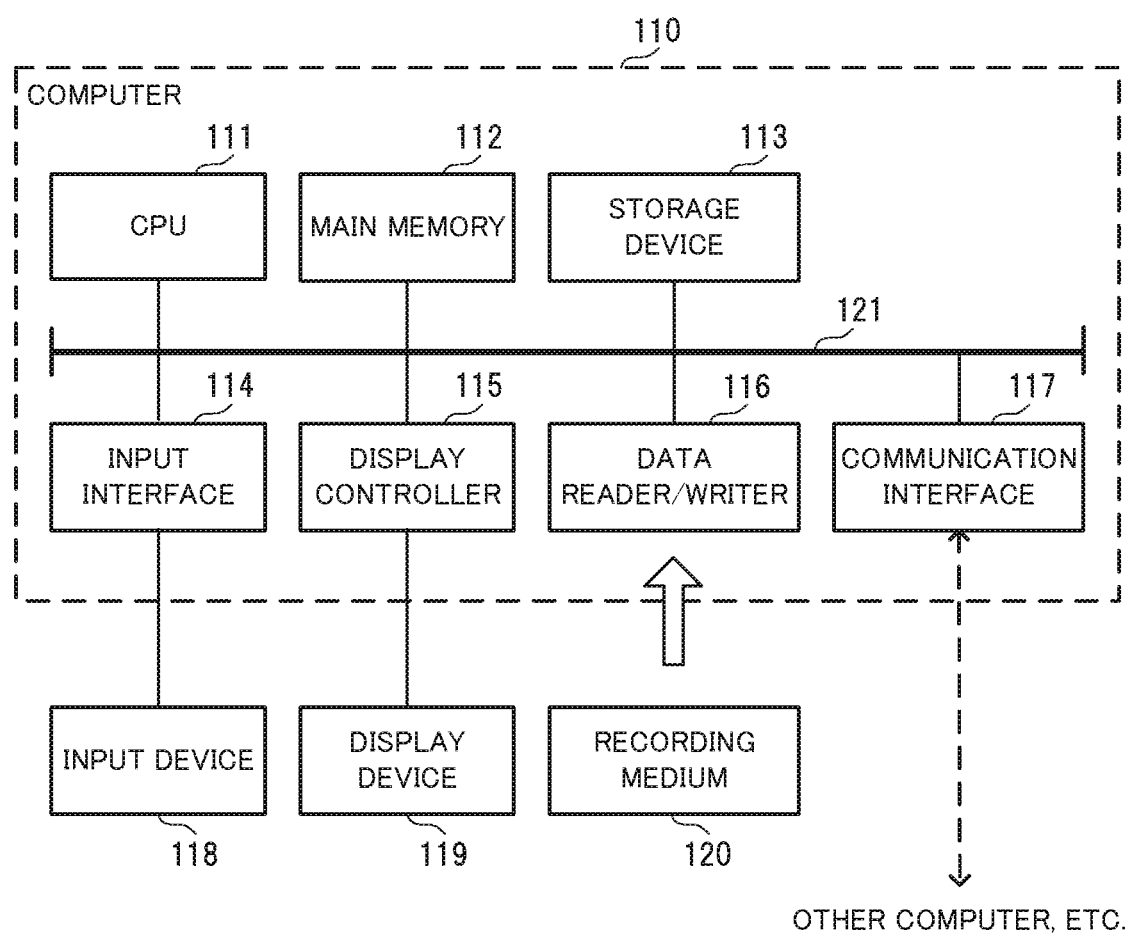
FIG. 11 is a block diagram showing an example of a computer that realizes the terminal apparatus and the server apparatus according to the example embodiment of the invention.

Here, an example of a computer capable of executing the first program or the second program according to the example embodiment will be described using FIG. 11. FIG. 11 is a block diagram showing an example of a computer that realizes the terminal apparatus and the server apparatus according to the example embodiment of the invention.

As shown in FIG. 11, a computer 110 includes a CPU (Central Processing Unit) 111, a main memory 112, a storage device 113, an input interface 114, a display controller 115, a data reader/writer 116, and a communication interface 117. These units are connected in a manner that enables data communication, via a bus 121. Note that the computer 110 may include a GPU (Graphics Processing Unit) or an FPGA (Field-Programmable Gate Array), in addition to the CPU 111 or instead of the CPU 111.

The CPU 111 implements various computational operations, by extracting programs (code) according to the example embodiment stored in the storage device 113 to the main memory 112, and executing these programs in predetermined order. The main memory 112, typically, is a volatile storage device such as a DRAM (Dynamic Random Access Memory). Also, programs according to the example embodiment are provided in a state of being stored on a computer-readable recording medium 120. Note that programs according to the example embodiment may be distributed over the Internet connected via the communication interface 117.

Also, a semiconductor storage device such as a flash memory is given as a specific example of the storage device 113, other than a hard disk drive. The input interface 114 mediates data transmission between the CPU 111 and input devices 118 such as a keyboard and a mouse. The display controller 115 is connected to a display device 119 and controls display by the display device 119.

The data reader/writer 116 mediates data transmission between the CPU 111 and the recording medium 120, and executes readout of programs from the recording medium 120 and writing of processing results of the computer 110 to the recording medium 120. The communication interface 117 mediates data transmission between the CPU 111 and other computers.

Also, a general-purpose semiconductor storage device such as a CF (Compact Flash (registered trademark)) card or an SD (Secure Digital) card, a magnetic recording medium such as a flexible disk, and an optical recording medium such as a CD-ROM (Compact Disk Read Only Memory) are given as specific examples of the recording medium 120.

Note that the server apparatus 10 and the terminal apparatus 20 according to the example embodiment are also respectively realizable by using hardware corresponding to the respective units, rather than by a computer on which programs are installed. Furthermore, the server apparatus 10 and the terminal apparatus 20 may respectively be realized in part by programs, and the remaining portion may be realized by hardware.

The example embodiment described above can be partially or wholly realized by supplementary notes 1 to 23 described below, but the invention is not limited to the following description.

(Supplementary Note 1)
A server apparatus configured to be communicably connected to a terminal apparatus for collecting sensor data from an odor sensor that outputs the sensor data in reaction to a plurality of types of odors, the server apparatus comprising:
an analyzer holding unit configured to hold a plurality of analyzers for analyzing specific odor analysis targets, based on the sensor data;
an analyzer management unit configured to select an analyzer capable of analyzing a designated odor analysis target, from among the plurality of analyzers, determine preprocessing to be performed on the sensor data, according to the selected analyzer, and cause the terminal apparatus to execute the determined preprocessing on the sensor data;
an analysis execution unit configured to, upon the preprocessed sensor data being transmitted thereto from the terminal apparatus, execute analysis processing of the designated odor analysis target, by applying the selected analyzer to the preprocessed sensor data transmitted thereto; and
an analysis result transmission unit configured to transmit information indicating a result of the analysis processing to the terminal apparatus.

(Supplementary Note 2)
The server apparatus according to supplementary note 1,
in which an analysis target and an accuracy at which to perform analysis are designated, via the terminal apparatus, and
the analyzer management unit is configured to select an analyzer capable of analyzing the designated analysis target and capable of achieving the designated accuracy, from among the plurality of analyzers.

(Supplementary Note 3)
The server apparatus according to supplementary note 2,
in which one or more odor analysis targets and the accuracy at which to perform analysis are designated by an application program that is executed in the terminal apparatus.

(Supplementary Note 4)
The server apparatus according to any of supplementary notes 1 to 3,
in which the analyzer management unit is configured to specify a feature amount to be extracted from the sensor data, according to the selected analyzer, determine processing for extracting the specified feature amount as preprocessing, and transmit a program module for executing the determined preprocessing to the terminal apparatus.

(Supplementary Note 5)
The server apparatus according to any of supplementary notes 1 to 4,
in which the analysis execution unit is configured to estimate a level of the designated analysis target from the result of the analysis processing, and
the analysis result transmission unit is configured to transmit information indicating the estimated level of the analysis target to the terminal apparatus, as the information indicating the result of the analysis processing.

(Supplementary Note 6)
A terminal apparatus for collecting sensor data from an odor sensor that outputs the sensor data in reaction to a plurality of types of odors and configured to be communicably connected to a server apparatus that holds a plurality of analyzers for analyzing specific odor analysis targets, based on the sensor data, the terminal apparatus including:
a sensor data collection unit configured to collect the sensor data;
a preprocessing unit configured to, in a case where, in the server apparatus, an analyzer capable of analyzing a designated odor analysis target is selected, from among the plurality of analyzers, and preprocessing to be performed on the sensor data is determined, according to the selected analyzer, execute the determined preprocessing on the collected sensor data;
a sensor data transmission unit configured to transmit the preprocessed sensor data to the server apparatus; and
an analysis result holding unit configured to, in a case where, in the server apparatus, analysis processing of the designated analysis target is executed, by the selected analyzer being applied to the preprocessed sensor data transmitted thereto, hold information indicating a result of the analysis processing.

(Supplementary Note 7)
The terminal apparatus according to supplementary note 6, further including:
a data reception unit configured to receive a designation of one or more odor analysis targets, and notify the designated one or more analysis targets to the server apparatus.

(Supplementary Note 8)
The terminal apparatus according to supplementary note 7, further including:
a program execution unit configured to execute an application program,
in which the data reception unit is configured to receive designations, by the application program, of one or more odor analysis targets and an accuracy at which to analyze the designated one or more odor analysis targets, and notify the designated one or more odor analysis targets and the designated accuracy to the server apparatus.

(Supplementary Note 9)
The terminal apparatus according to any of supplementary notes 6 to 8,
in which the preprocessing unit is configured to, in a case where, in the server apparatus, a feature amount to be extracted from the sensor data is specified, according to the selected analyzer, processing for extracting the specified feature amount is determined as preprocessing, and a program module for executing the determined preprocessing is transmitted therefrom, execute the determined preprocessing by executing the program module.

(Supplementary Note 10)

The terminal apparatus according to supplementary note 7, in which the data reception unit is configured to, in a case where information other than a name of an odor analysis target is received, specify a substance related to the received information and take the specified substance as the odor analysis target.

(Supplementary Note 11)

The terminal apparatus according to any of supplementary notes 6 to 10, in which the analysis result holding unit is configured to, in a case where, in the server apparatus, a level of the designated odor analysis target is estimated from the result of the analysis processing of the designated odor analysis target, display the estimated level on a screen, as the information indicating the result of the analysis processing.

(Supplementary Note 12)

An odor sensor data analysis method that uses a terminal apparatus for collecting sensor data from an odor sensor that outputs the sensor data in reaction to a plurality of types of odors and a server apparatus configured to be communicably connected to the terminal apparatus, the method comprising:

(a) a step of, with the terminal apparatus, collecting the sensor data;

(b) a step of, with the server apparatus, selecting an analyzer capable of analyzing a designated odor analysis target, from among a plurality of analyzers for analyzing specific odor analysis targets by analyzing the sensor data, and determining preprocessing to be performed on the sensor data, according to the selected analyzer;

(c) a step of, with the terminal apparatus, executing the determined preprocessing on the sensor data;

(d) a step of, with the terminal apparatus, transmitting the preprocessed sensor data to the server apparatus;

(e) a step of, with the server apparatus, executing analysis processing of the designated odor analysis target, by applying the selected analyzer to the preprocessed sensor data transmitted thereto from the terminal apparatus;

(f) a step of, with the server apparatus, transmitting information indicating a result of the analysis processing to the terminal apparatus; and (g) a step of, with the terminal apparatus, holding the information indicating the result of the analysis processing.

(Supplementary Note 13)

A computer-readable recording medium that includes a program recorded thereon, the program including instructions that cause a computer configured to be communicably connected to a terminal apparatus for collecting sensor data from an odor sensor that outputs the sensor data in reaction to a plurality of types of odors to carry out:

(a) a step of holding a plurality of analyzers for analyzing specific odor analysis targets, based on the sensor data;

(b) a step of selecting an analyzer capable of analyzing a designated odor analysis target, from among the plurality of analyzers, determining preprocessing to be performed on the sensor data, according to the selected analyzer, and causing the terminal apparatus to execute the determined preprocessing on the sensor data;

(c) a step of, upon the preprocessed sensor data being transmitted thereto from the terminal apparatus, executing analysis processing of the designated odor analysis target, by applying the selected analyzer to the preprocessed sensor data transmitted thereto; and (d) a step of transmitting information indicating a result of the analysis processing to the terminal apparatus.

(Supplementary Note 14)

The computer-readable recording medium according to supplementary note 13, in which an analysis target and an accuracy at which to perform analysis are designated, via the terminal apparatus, and in the (b) step, an analyzer capable of analyzing the designated analysis target and capable of achieving the designated accuracy is selected, from among the plurality of analyzers.

(Supplementary Note 15)

The computer-readable recording medium according to supplementary note 14, in which one or more odor analysis targets and the accuracy at which to perform analysis are designated by an application program that is executed in the terminal apparatus.

(Supplementary Note 16)

The computer-readable recording medium according to any of supplementary notes 13 to 15, in which, in the (b) step, a feature amount to be extracted from the sensor data is specified, according to the selected analyzer, processing for extracting the specified feature amount is determined as preprocessing, and a program module for executing the determined preprocessing is transmitted to the terminal apparatus.

(Supplementary Note 17)

The computer-readable recording medium according to any of supplementary notes 13 to 16, in which, in the (c) step, a level of the designated analysis target is estimated from the result of the analysis processing, and in the (d) step, information indicating the estimated level of the analysis target is transmitted to the terminal apparatus, as the information indicating the result of the analysis processing.

(Supplementary Note 18)

A computer-readable recording medium that includes a program recorded thereon, the program including instructions that cause a computer for collecting sensor data from an odor sensor that outputs the sensor data in reaction to a plurality of types of odors and configured to be communicably connected to a server apparatus that holds a plurality of analyzers for analyzing specific odor analysis targets based on the sensor data to carry out:

(a) a step of collecting the sensor data;

(b) a step of, in a case where, in the server apparatus, an analyzer capable of analyzing a designated odor analysis target is selected, from among the plurality of analyzers, and preprocessing to be performed on the sensor data is determined, according to the selected analyzer, executing the determined preprocessing on the collected sensor data;

(c) a step of transmitting the preprocessed sensor data to the server apparatus; and (d) a step of, in a case where, in the server apparatus, analysis processing of the designated analysis target is executed, by the selected analyzer being applied to the preprocessed sensor data transmitted thereto, holding information indicating a result of the analysis processing.

(Supplementary Note 19)

The computer-readable recording medium according to supplementary note 18, in which the program further includes instructions that cause the computer to carry out:

(e) a step of receiving a designation of one or more odor analysis targets, and notifying information of the designated one or more odor analysis targets to the server apparatus.

(Supplementary Note 20)

The computer-readable recording medium according to supplementary note 19, in which the program further includes instructions that cause the computer to carry out:

(g) a step of executing an application program, and in the (e) step, designations, by the application program, of one or more odor analysis targets and an accuracy at which to analyze the designated one or more odor analysis targets are received, and the designated one or more odor analysis targets and the designated accuracy are notified to the server apparatus.

(Supplementary Note 21)

The computer-readable recording medium according to any of supplementary notes 18 to 20, in which, in the (b) step, in a case where, in the server apparatus, a feature amount to be extracted from the sensor data is specified, according to the selected analyzer, processing for extracting the specified feature amount is determined as preprocessing, and a program module for executing the determined preprocessing is transmitted therefrom, the determined preprocessing is executed by executing the program module.

(Supplementary Note 22)

The computer-readable recording medium according to supplementary note 19, in which, in the (e) step, in a case where information other than a name of a substance that serves as an odor analysis target is received, a substance related to the received information is specified and the specified substance is taken as the odor analysis target.

(Supplementary Note 23)

The computer-readable recording medium according to any of supplementary notes 18 to 22, in which, in the (d) step, in a case where, in the server apparatus, a level of the designated odor analysis target is estimated from the result of the analysis processing of the designated odor analysis target, the estimated level of the odor is held and the estimated level of the odor is displayed on a screen, as the information indicating the result of the analysis processing.

Although the invention of the present application has been described above with reference to an example embodiment, the invention is not limited to the example embodiment described above. Various modifications apparent to those skilled in the art can be made to the configurations and details of the invention within the scope of the invention.

This application is based upon and claims the benefit of priority from Japanese application No. 2017-193901, filed on Oct. 3, 2017, the disclosure of which is incorporated herein in its entirety by reference.

INDUSTRIAL APPLICABILITY

As described above, according to the invention, in the case where edge computing is applied to an odor sensor whose odor analysis target is not fixed, it becomes possible to analyze odors, without increasing the load on the system. The invention is useful in various fields in which odor sensors are utilized.

LIST OF REFERENCE SIGNS

10 Server apparatus
11 Analyzer holding unit
12 Analyzer management unit
13 Analysis execution unit
14 Analysis result transmission unit
20 Terminal apparatus
21 Sensor data collection unit
22 Preprocessing unit
23 Sensor data transmission unit
24 Analysis result holding unit
25 Program execution unit
26 Data reception unit
27 Display device
28 Operation button
29 Window
30 System
40 Odor sensor
41 Environmental sensor
44 Sensor unit
110 Computer
111 CPU
112 Main memory
113 Storage device
114 Input interface
115 Display controller
116 Data reader/writer
117 Communication interface
118 Input device
119 Display device
120 Recording medium
121 Bus

The invention claimed is:

1. A server apparatus configured to be communicably connected to a terminal apparatus for collecting sensor data from a Membrane-type Surface Stress (MSS) odor sensor that outputs the sensor data in reaction to a plurality of types of odors, the server apparatus comprising:

a processor; and memory storing executable instructions that, when executed by the processor, causes the processor to perform as:

an analyzer holding unit configured to hold a plurality of analysis models created by machine learning for analyzing specific odor analysis targets, based on the sensor data;

an analyzer management unit configured to select an analysis model capable of analyzing a designated odor analysis target, from among the plurality of analysis models, determine preprocessing to be performed on the sensor data, according to the selected analysis model, and cause the terminal apparatus to execute the determined preprocessing on the sensor data;

an analysis execution unit configured to, upon the preprocessed sensor data being transmitted thereto from the terminal apparatus, execute analysis processing of the designated odor analysis target, by applying the selected analysis model to the preprocessed sensor data transmitted thereto; and an analysis result transmission unit configured to transmit information indicating a result of the analysis processing to the terminal apparatus.

2. The server apparatus according to claim 1, wherein an analysis target and an accuracy at which to perform analysis are designated, via the terminal apparatus, and the analyzer management unit is configured to select an analysis model capable of analyzing the designated analysis target and capable of achieving the designated accuracy, from among the plurality of analysis models.

3. The server apparatus according to claim 2,
wherein one or more odor analysis targets and the accuracy at which to perform analysis are designated by an application program that is executed in the terminal apparatus.

4. The server apparatus according to claim 1,
wherein the analyzer management unit is configured to specify a feature amount to be extracted from the sensor data, according to the selected analysis model, determine processing for extracting the specified feature amount as preprocessing, and transmit a program module for executing the determined preprocessing to the terminal apparatus.

5. The server apparatus according to claim 1,
wherein the analysis execution unit is configured to estimate a level of the designated odor analysis target from the result of the analysis processing, and
the analysis result transmission unit is configured to transmit information indicating the estimated level of the odor analysis target to the terminal apparatus, as the information indicating the result of the analysis processing.

6. An odor sensor data analysis method that uses a terminal apparatus for collecting sensor data from a Membrane-type Surface Stress (MSS) odor sensor that outputs the sensor data in reaction to a plurality of types of odors and a server apparatus configured to be communicably connected to the terminal apparatus, the method comprising:
with the terminal apparatus, collecting the sensor data;
with the server apparatus, selecting an analysis model capable of analyzing a designated odor analysis target, from among a plurality of analysis models created by machine learning for analyzing specific odor analysis targets by analyzing the sensor data, and determining preprocessing to be performed on the sensor data, according to the selected analysis model;
with the terminal apparatus, executing the determined preprocessing on the sensor data;
with the terminal apparatus, transmitting the preprocessed sensor data to the server apparatus;
with the server apparatus, executing analysis processing of the designated odor analysis target, by applying the selected analysis model to the preprocessed sensor data transmitted thereto from the terminal apparatus;
with the server apparatus, transmitting information indicating a result of the analysis processing to the terminal apparatus; and
with the terminal apparatus, holding the information indicating the result of the analysis processing.

7. A non-transitory computer-readable recording medium that includes a program recorded thereon, the program including instructions that cause a computer configured to be communicably connected to a terminal apparatus for collecting sensor data from a Membrane-type Surface Stress (MSS) odor sensor that outputs the sensor data in reaction to a plurality of types of odors to carry out:
holding a plurality of analysis models created by machine learning for analyzing specific odor analysis targets, based on the sensor data;
selecting an analysis model capable of analyzing a designated odor analysis target, from among the plurality of analysis models, determining preprocessing to be performed on the sensor data, according to the selected analysis model, and causing the terminal apparatus to execute the determined preprocessing on the sensor data;
upon the preprocessed sensor data being transmitted thereto from the terminal apparatus, executing analysis processing of the designated odor analysis target, by applying the selected analysis model to the preprocessed sensor data transmitted thereto; and
transmitting information indicating a result of the analysis processing to the terminal apparatus.

8. The non-transitory computer-readable recording medium according to claim 7,
wherein an analysis target and an accuracy at which to perform analysis are designated, via the terminal apparatus, and
an analyzer capable of analyzing the designated analysis target and capable of achieving the designated accuracy is selected, from among the plurality of analysis models.

9. The non-transitory computer-readable recording medium according to claim 8,
wherein one or more odor analysis targets and the accuracy at which to perform analysis are designated by an application program that is executed in the terminal apparatus.

10. The non-transitory computer-readable recording medium according to claim 7,
wherein, a feature amount to be extracted from the sensor data is specified, according to the selected analysis models, processing for extracting the specified feature amount is determined as preprocessing, and a program module for executing the determined preprocessing is transmitted to the terminal apparatus.

11. The non-transitory computer-readable recording medium according to claim 7,
wherein, a level of the designated analysis target is estimated from the result of the analysis processing, and
information indicating the estimated level of the analysis target is transmitted to the terminal apparatus, as the information indicating the result of the analysis processing.

12. A non-transitory computer-readable recording medium that includes a program recorded thereon, the program including instructions that cause a computer for collecting sensor data from a Membrane-type Surface Stress (MSS) odor sensor that outputs the sensor data in reaction to a plurality of types of odors and configured to be communicably connected to a server apparatus that holds a plurality of analysis models created by machine learning for analyzing specific odor analysis targets based on the sensor data to carry out:
collecting the sensor data;
in a case where, in the server apparatus, an analysis model capable of analyzing a designated odor analysis target is selected, from among the plurality of analysis models, and preprocessing to be performed on the sensor data is determined, according to the selected analysis model, executing the determined preprocessing on the collected sensor data;
transmitting the preprocessed sensor data to the server apparatus; and
in a case where, in the server apparatus, analysis processing of the designated analysis target is executed, by the selected analysis model being applied to the preprocessed sensor data transmitted thereto, holding information indicating a result of the analysis processing.

13. The non-transitory computer-readable recording medium according to claim 12, wherein the program further includes instructions that cause the computer to carry out:

receiving a designation of one or more odor analysis targets, and notifying information of the designated one or more odor analysis targets to the server apparatus.

14. The non-transitory computer-readable recording medium according to claim 13, wherein the program further includes instructions that cause the computer to carry out:

executing an application program, and designations, by the application program, of one or more odor analysis targets and an accuracy at which to analyze the designated one or more odor analysis targets are received, and the designated one or more odor analysis targets and the designated accuracy are notified to the server apparatus.

15. The non-transitory computer-readable recording medium according to claim 13, wherein, in a case where information other than a name of a substance that serves as an odor analysis target is received, a substance related to the received information is specified and the specified substance is taken as the odor analysis target.

16. The non-transitory computer-readable recording medium according to claim 12, wherein, in a case where, in the server apparatus, a feature amount to be extracted from the sensor data is specified, according to the selected analysis models, processing for extracting the specified feature amount is determined as preprocessing, and a program module for executing the determined preprocessing is transmitted therefrom, the determined preprocessing is executed by executing the program module.

17. The non-transitory computer-readable recording medium according to claim 12, wherein, in a case where, in the server apparatus, a level of the designated odor analysis target is estimated from the result of the analysis processing of the designated odor analysis target, the estimated level of the odor is held and the estimated level of the odor is displayed on a screen, as the information indicating the result of the analysis processing.

\* \* \* \* \*